US006005077A

United States Patent [19]
Schwarz et al.

[11] Patent Number: 6,005,077
[45] Date of Patent: Dec. 21, 1999

[54] USE OF VON WILLEBRAND FACTOR AND PHARMACEUTICAL FORMULATION

[75] Inventors: Hans-Peter Schwarz, Vienna; Peter Turecek, Klosterneuburg; Johann Eibl, Vienna, all of Austria

[73] Assignee: Immuno Aktiengesellschaft, Vienna, Austria

[21] Appl. No.: 08/744,646

[22] Filed: Nov. 6, 1996

[30] Foreign Application Priority Data

Nov. 10, 1995 [DE] Germany .......................... 195 42 004
Apr. 25, 1996 [DE] Germany .......................... 196 16 540

[51] Int. Cl.$^6$ .................................................. A61K 35/14
[52] U.S. Cl. ............................ 530/383; 514/12; 435/68.1
[58] Field of Search ............................. 530/383; 514/12; 435/68.1

[56] References Cited

U.S. PATENT DOCUMENTS

| | | | |
|---|---|---|---|
| 4,455,301 | 6/1984 | Mitra et al. | 424/101 |
| 5,408,039 | 4/1995 | Burnouf-Radosevich et al. | 530/383 |
| 5,597,711 | 1/1997 | Zimmerman et al. | 435/69.9 |
| 5,618,788 | 4/1997 | Capon et al. | 514/12 |

FOREIGN PATENT DOCUMENTS

| | | |
|---|---|---|
| 0 131 740 | 1/1985 | European Pat. Off. . |
| 0 159 311 | 10/1985 | European Pat. Off. . |
| 0 197 592 | 10/1986 | European Pat. Off. . |
| 0197592B1 | 10/1986 | European Pat. Off. . |
| 0469985A1 | 2/1992 | European Pat. Off. . |
| 0 519 901 | 12/1992 | European Pat. Off. . |
| 0 705 846 | 4/1996 | European Pat. Off. . |
| 44 34 538 | 4/1995 | Germany . |
| 4435485C1 | 3/1996 | Germany . |
| 90/15613 | 12/1990 | WIPO . |
| WO91/06314 | 5/1991 | WIPO . |
| WO96/10584 | 4/1996 | WIPO . |

OTHER PUBLICATIONS

Schlokat et al. (1995) Thrombosis and Hemostasis vol. 73, No. 6, Abstract No. 993, 1995.
Drouet et al. (1995) Blood 86/10, 1995.
Goudemand et al. (1992) British J. Haematology 80:214–221, 1992.
Burnouf–Radosevich et al., Vox Sang 62: 1–11 (1992).
Andrews et al., Biochemistry 28: 8326–8336 (1989).
Titani et al., Biochemistry 25: 3171–3184 (1986).
Mancuso et al., J. Biological Chemistry 264(33): 19514–19527 (1989).
Thrombosis and Haemostatsis/Abstracts 73(6): 1160, Abstract 993 (1995).
Drouet et al. Blood 86(10) (1995).
Goudemand et al. British Journal of Haematology 80:214–221 (1992).
Lethagen et al. Annals of Hematology 65(6): 253–259 (1992).
Mannucci et al., "Proteolysis of von Willerbrand Factor in Theraeutic Plasma Concentrates", Blood, vol. 83, No. 10, (1994), pp. 3018–3027.

Fischer et al., "Structural Analysis of Recombinant von Willerbrand Factor: Identification of Hetero–and Homo–Dimers", Federation of European Biochemical Societies Letters, vol. 351, (1994), pp. 345–348.
Weiss et al., "Quantitative Assay of Plasma Factor Deficient in Von Willerbrand's Disease that is Necessary for Platelet Aggregation", J. Clinical Investigation, vol. 52, (1973), pp. 2708–2716.
Fricke et al., "Standards for Assay of von Willebrand Factor Concentrates: A Collaborative Study", Thrombosis and Haemostasis, vol. 70, No. 2, (1993), pp. 351–356.
Sadler et al., "Molecular Mechanism and Classification of von Willebrand Disease", Thrombosis and Homeostasis, vol. 74, No. 1, (1993), pp. 161–166.
Wagner et al., "Inhibition of Disulfide Bonding of von Willebrand Protein by Monensin Results in Small, Functionally Defective Multimers", J. Cell Biol., vol. 101, No. 1, (1985), pp. 112–120.
van Ouweland et al., "Structural Homology Between the Human Fur Gene Product and the Subtilisin–Like Protease Encoded by Yeast KEX2", Nucleic Acids Research. vol. 18, No. 3 (1990).
Bluml et al., "Protein Free Culture of R–CHO and Hybridoma Cells on the Macroporous Polypore Carrier", Animal Cell Tech., (1994), pp. 267–269.
Evans et al., "Assay of Ristocetin Co–Factor Using Fixed Platelets and A Platelet Counting Technique", British Journal of Haematology, vol. 37, (1977), pp. 289–294.
Roussi et al., "Absence of Incorporation of Plasma on Willebrand Factor Into Porcine Platelet –A–Granules", Bristish Journal of Haematology, vol. 90, (1995), pp. 661–668.
Samama et al., "Aprotinin Could Promote Arterial Thrombosis in Pigs: A Prospective Randomized, Blind Study", Thrombosis and Haemostasis, vol. 71, (1994), pp. 661–668.
Ruggeri et al., "The Complex Multimeric Composition of Factor VIII/von Willebrand Factor", Blood, vol. 57, No. 6, (1981), pp. 1140–1143.
Aihara et al., "Visualization of von Willebrand Factor Multimers by Immunoenzymatic Strain Using Avidin–Biotin Peroxidasae Complex", Thrombosis and Haemostasis, vol. 55, (1986), pp. 263–267.
Novak et al., "Coca:a New Mouse Model for Platelet Storage Pool Deficiency", British Journal of Haematology, vol. 69, (1988), pp. 371–378.
Bradford, "A Rapid and Sensitive Method for the Quantiation of Microgram Quantities of Protein Utilizing the Principle of Protein–Dye Binding", Anal. Biochem., vol. 72, (1976), pp. 248–254.
"Thrombosis and Haemostasis", vol. 73, (1995), pp. 1160.

*Primary Examiner*—Bradley L. Sisson
*Assistant Examiner*—Enrique D. Longton
*Attorney, Agent, or Firm*—Foley & Lardner

[57] ABSTRACT

The invention relates to the use of von Willebrand Factor (vWF) with a prolonged biological half-life for the production of a preparation for stabilization of blood coagulation Factor VIII (FVIII:C) in a mammal. Additionally, a pharmaceutical preparation is provided comprising a biologically active FVIII:C/vWF complex with improved pharmokinetic properties, said complex containing a vWF with a prolonged biological half-life.

15 Claims, 7 Drawing Sheets

MOUSE goat anti-FVIII/vWF inhibitor plasma
(10 ml/kg, i.v., bolus)

↓ 30 min injection of the test substance
(15 ml/kg, i.v., bolus)

↓ 20 min narcosis

↓ tail end bleeding

MOUSE goat anti-vWF inhibitor plasma
(10 ml/kg, i.v., bolus)

↓ 24 h injection of the test substance
(15 ml/kg, i.v., bolus)

↓ 20 min narcosis

↓ tail end bleeding

USE OF VON WILLEBRAND FACTOR AND PHARMACEUTICAL FORMULATION

This application claims section 119 priority from Fed. Rep. of Germany 195 42 004.7 filed Nov. 10, 1995 and Fed. Rep. of Germany 196 16 540.7 filed Apr. 25, 1996.

The invention relates to a pharmaceutical preparation containing a biologically active FVIII:C/vWF complex as well as a new use of a von Willebrand Factor preparation and a diagnostic kit for determining a defect in hemostasis in a patient.

BACKGROUND OF THE INVENTION vWF is present in human plasma as a heterogeneous homo-multimer with a molecular weight of 450 kD to more than 10,000 kD. vWF serves as a carrier protein for coagulation factor VIII and contributes to adhesion of blood platelets to the endothelium of injured blood vessels.

In hemophilia, blood coagulation is disturbed by a lack of certain plasmatic blood coagulation factors. In hemophilia A, the tendency to hemorrhage is based on a lack of Factor VIII and/or a lack of vWF. Hemophilia A is treated through replacement of the missing coagulation factor by factor concentrates of conserved blood, for example by intravenous infusion of Factor VIII, a vWF/Factor VIII complex or vWF.

There are several syndromes which are associated with the underproduction or overproduction of von Willebrand Factor. Thus, an overproduction of vWF leads, for example, to an increased tendency of thrombosis, whereas an insufficient supply of vWF results in an increased tendency to hemorrhage or in prolonged bleeding time.

von Willebrand's syndrome can be manifested as several types. All forms are distinguished by a prolonged bleeding time which can be accounted for by an absolute lack of a functional vWF. The lack of vWF can also cause a phenotypic hemophilia A because vWF is an essential component of the functional Factor VIII complex. In these cases, the half-life of Factor VIII is decreased in such a manner that it cannot assert its specific functions in blood coagulation.

Patients with vW disease have a lack of functionally active vWF as a cause of hemorrhages. For therapy of vW disease, therapeutic plasma concentrates which contain vWF are proposed above all. However, the vWF originating from plasma (pdvWF) has an altered multimer distribution. The high molecular multimers are degraded during the manufacturing process for which reason a decreased hemostatic action of the plasma concentrates is presumed. Soluble proteases and/or proteases bound to blood platelets or leukocytes are considered to be primarily responsible for the degradation of high-molecular vWF multimers (Mannucci et al. Blood 83, 3018–3027 (1994)).

For prevention of problems which are associated with the production of pdvWF, the production of recombinant vWF (rvWF) by fermentation of recombinant cells has already been proposed. Fischer et al. (FEBS Letters 351, 345–348 (1994)) describe the expression of wild-type vWF in CHO cells. The cDNA for vWF has been described in EP 0 197 592. The rvWF produced was examined for its molecular structure. A gel electrophoretic examination showed that the multimer structure of rvWF corresponds with the ideal structure of pdvWF, whereby the high-molecular structure could also be detected. However, it was found that the rvWF is not separated into the triplet structure which is characteristic for pdvWF. This triplet structure comprises a predominant band and two or more satellite bands which occur in a complex with the predominant band of pdvWF.

The large-scale production of rvWF is described by Schlokat et al. (Thrombosis and Haemostasis 73, abstr. 993 (1995)). The rvWF produced in CHO cells was chromatographically purified, whereby no reduction of the specific ristocetin cofactor activity occurred. The processing of the pro-protein to mature rvWF was attained by co-expression of the enzyme furin. The obtained ristocetin cofactor activity was relatively high for all examined clones, for example, 70 units per unit vWF antigen.

The ristocetin cofactor activity of vWF is typically determined according to the instructions of Weiss et al. (Journal of Clinical Investigation 52, 2708–2716 (1973)). Thereby, the activity of vWF as a cofactor for the ristocetin-induced aggregation of blood platelets is examined.

This activity serves as a measure for the effectiveness of vWF for treatment of vW disease. From Fricke et al. (Thrombosis and Haemostasis 70, 351–356 (1993)) a very high ratio of 0.92 ristocetin-cofactor activity (RCoF) to vWF antigen (vWF:Ag) was found for Factor VIII and vWF in a plasma standard of the World Health Organization (WHO).

The vWF preparations described in the art contain vWF in proteolytically degraded form. Therefore, the stability of these preparations is limited. Attempts to prevent the proteolysis after drawing a blood sample in the presence of suitable inhibitors also did not lead to a vWF with intact structure.

Additionally, all vWF concentrates that are obtained by purification of the protein from human blood plasma or are separated in contact with biological material from mammals are potentially at risk of containing pathogenic molecules from plasma donors, such as for example, viruses.

A further problem for state of the art vWF preparations constitutes the short half-life of vWF after administration to a patient. In this connection, a decreased half-life of FVIII:C was also determined. The half-life for exogenous FVIII:C generally lies below that of endogenous FVIII:C, in the case of plasmatic FVIII:C typically approximately 10 h, and in the case of recombinant FVIII:C not more than approximately 12 h.

Thus, the half-life for a FVIII:C/vWF concentrate from the Centre Regional de Transfusion Sanguine de Lille (France) according to the product description 1992 lies at 10 to 14 h; after administration of this preparation, an increase in the endogenous FVIII:C to merely to 1 to 3 units per milliliter in 24 hours could be observed. For another FVIII:C/vWF-containing preparation (Haemate® HS Behring), the half-life is given as 7 hours in type 3 vW disease, 12.3 h in type 2A and 13.8 h in type 1.

SUMMARY OF THE INVENTION

An object of the invention is to widen the indication spectrum for vWF and to attain improved pharmacokinetics of Factor VIII in vivo.

These and other objects are accomplished by the present invention, which encompasses biotechnology inventions, including biotechnology processes. In accordance with one aspect of the present invention, there are provided pharmaceutical preparations for persistent increase of the blood coagulation Factor VIII level in a mammal comprising von Willebrand Factor (vWF) and/or a vWF fraction with a prolonged biological half-life. Preferably, the pharmaceutical preparation comprises vWF and/or a vWF fraction that has an in vivo half-life of more than 20 hours, and has a multimer structure consisting of singlets. Preferably, the vWF and/or the vWF fraction has the entire spectrum of multimers similar to the native multimer distribution, including those with high molecular weight. Suitable fractions include those comprising low molecular vWF having a molecular weight of lower than 5 million daltons, preferably lower than 3 million daltons.

The pharmaceutical preparation according to the invention can be in a ready-to-administer solution that contains vWF and/or a vWF fraction in a concentration in the range of 1 to 1,000 U/ml. The vWF and/or the vWF fraction can be chromatographically purified.

The pharmaceutical preparation can comprise recombinant vWF (rvWF) and/or a fraction of rvWF. Preferably, the pharmaceutical preparation comprises rvWF and/or the rvWF fraction that is at least 80%, preferably more than 90% to 100%, proteolytically processed by contact with a protease.

The pharmaceutical preparation according to the present invention also can comprise FVIII:C, including recombinant FVIII:C. The vWF and/or the vWF fraction can be completed with factor VIII. The Factor VIII preferably is biologically active, and can be a native protein and/or a functional agent, a mutant or a derivative thereof. Preferably, the FVIII:C has an in vivo half-life of more than 13 hours, preferably more than 17 hours.

The present invention also includes methods for stabilizing blood coagulation factor VIII (FVIII:C) in a mammal, which comprises administering to the mammal a pharmaceutical preparation as described above. The preparation can be suitable for increasing the endogenous content of FVIII:C and/or stabilizing FVIII:C concentration over a time period of about 24 hours, 48 hours or more. The mammal can be a patient with congenital or acquired lack of functional vWF. Additionally, the mammal can be a patient who suffers from functional disorders of vWF, such as von Willebrand's disease. Moreover, the mammal can be a patient who has antibodies against vWF and/or FVIII:C, or a patient who suffers from phenotypic hemophilia A. Preferably, the preparation according to the invention is repeatedly administered to said mammal in intervals of more than about 12 hours, such as daily administration. Additionally, the FVIII:C also can be administered.

The present invention also includes methods for the production of a preparation for determination of phenotypic hemophilia A, wherein the preparation is produced using vWF and/or a vWF fraction. The preparation can comprise vWF and/or a vWF fraction, including rvWF, preferably with a half-life of at least about 20 hours. The method can be capable of differentiating von Willebrand disease from a disease with simultaneous occurrence of a genomic defect resulting in a lack of FVIII:C, such as hemophilia A.

The present invention also includes diagnostics kit for determination of phenotypic hemophilia A, comprising (a) vWF and/or a vWF fraction in a pharmaceutically acceptable form and (b) n agent for determining FVIII:C activity in a blood sample of the patient. A diagnostic kit can include a vWF and/or a vWF fraction that is free of FVIII:C activity. Preferably, the vWF and/or the vWF fraction, including rvWF, has a half-life of at least about 20 hours. The agent for determination of FVIII:C activity according to the present invention can comprise a reagent that contains an activator of blood coagulation and an agent for detection of blood coagulation. According to the present invention, the agent for detection of blood coagulation can comprise a chromogenic substrate which is specific for factor Xa.

DETAILED DESCRIPTION OF THE INVENTION

It was surprisingly found that FVIII:C in vivo can be particularly well stabilized and stabilized in a long-lasting manner when a vWF with the high half-life of more than 20 h, preferably at least 30 h is employed. Not only native human vWF, but also functional analogs, derivatives, fragments and mutants can be provided as effective components. Preferably, recombinant vWF (rvWF) is employed according to the invention. It is further preferred to provide a vWF fraction in the preparation according to the invention. The vWF can be fractionated by chromatographic purification methods, especially by ion exchange and/or affinity chromatography, whereby fractions can be isolated which show a long half-life and/or lasting and persistent increase of the Factor VIII level in vivo.

It has been surprisingly determined that FVIII:C is not only stabilized by the administration of a vWF with prolonged half-life, but also that FVIII:C is endogenously induced in a persistent manner. The induction of endogenous FVIII:C plays a role, above all, when the organism should not be burdened with exogenous FVIII:C. In the case of a vW disease, a lack of FVIII:C is often simultaneously found although the patient does not suffer from hemophilia A (pseudo-hemophilia). Therefore, the administration of FVIII:C would not be absolutely necessary if sufficient endogenous FVIII:C is produced by the administration of vWF.

One type of pseudo hemophilia is attributed to mutations in the vWF molecule in the region between 1 and 272 which negatively influences the binding of FVIII:C. For example, in the case of vWF Normandi, a point mutation is responsible for the absent binding capacity for FVIII:C.

Consequently, a vWF with a prolonged half-life is suitable for use according to the invention on a human patient with cogenital or acquired lack of functional vWF. According to the invention, the following diseases and/or conditions caused by the diseases according to the classification of Sadler et al., Thromb. Haemostasis 74:161–166 (1995) are especially treated. All vWF diseases in the case of mutations of the vWF molecule, but also the vWF diseases of type 1, 2 and 3 which are characterized by a lack of vWF, are found among these. These diseases are to be subsumed under the concept of functional disorders of vWF.

In a particular embodiment, disease states are treated which are associated with the occurrence of antibodies against vWF and/or FVIII:C. A further preferred embodiment relates to the treatment of a patient who suffers from phenotypic hemophilia A.

The methods according to the invention can be used in therapeutic and phophylactic contexts. The term "treating" in its various grammatical forms in relation to the present invention refers to preventing, curing, reversing, attenuating, alleviating, minimizing, suppressing or halting the deleterious effects of a disease state, disease progression or other abnormal condition. A preparation comprising vWF with a prolonged half-life is especially suitable for prophylaxis, for example before a possible injury to the patient or before an operation which lasts several hours.

Thereby, the administration of vWF can be combined with or without administration of FVIII:C depending on the type of disease. A FVIII:C content in the pharmaceutical preparation is desirable, above all, when an acute hemorrhage should be quickly alleviated. Because the increase of endogenous FVIII:C content in the blood of the patient is only relevant after several hours, an initial administration of FVIII:C together with vWF is to be preferred.

The provision of a pharmaceutical preparation comprising FVIII:C and vWF for use according to the invention has the advantage that the FVIII:C is not only stabilized in vivo, but also in vitro. The combination with FVIII:C as a native protein or a suitable functional agent, a derivative, analoge or mutants is particularly advantageous, especially in the case of rvWF. The stability of the employed preparation is relevant, above all, for infusion preparations which can be infused into a patient over a period of several hours without the risk of alteration of the preparation and the necessity of changing the dosage scheme.

It has been surprisingly determined that vWF with a prolonged half-life substantially improves the pharmacokinetic properties of FVIII:C. Thus, according to the invention, a preparation can also be provided which comprises biologically active FVIII:C/vWF complex which improved pharmacokinetic properties, such as a high in vivo recovery (recovery or biological availability) and/or an increased half-life in vivo for the FVIII:C, are resulting, above all, from the content of vWF with a prolonged half-life. The FVIII:C/vWF preparation according to the invention generally shows a biological half-life of FVIII:C of more than 13 h, especially more than 17 h, whereby half-lives of more than 25 h are possible. The in vivo recovery of the preparation according to the invention in plasma is typically in a range of 90 to 100%.

The FVIII:C increase after administration of vWF with increased half-life can induce up to 6 units per milliliter or more, whereas it could be confirmed in controlled experiments that merely 3 units per milliliter were obtained by administration of Haemate® HS Behring in animal studies.

For the use according to the invention, the mature form of vWF which is proteolytically processed to a large extent is suitable above all. Preferably, rvWF is used which is at least 80%, most preferably more than 90 up to 100%, proteolytically processed by contact with a protease, such as for example, furin or a protease of the subtilisin type.

According to the invention, vWF is administered in a manner and concentration such that the FVIII:C is stabilized in vivo over a period of at least 48 hours, preferably more than 72 hours. The FVIII:C content in vivo is considered as stable when at least 0.1, preferably more than 0.3 units per milliliter blood, is contained despite elimination of endogenous and/or exogenous FVIII:C. This minimal content of FVIII:C guarantees a minimal protection of the patient against undesirable hemorrhages.

In accordance with the long-lasting and persistent effect of the vWF in vivo, the initial dose can be decreased so that the pharmaceutical preparation according to the invention can be administered to a patient without side-effect reactions such as thrombosis formation, thrombocyte activation or thrombocytopenia.

The preparation can be administered several times, whereby longer intervals are possible due to the long half-life of the vWF, for example intervals of more than 12 hours, preferably approximately 24 hours (daily administration). The effective vWF amount in the pharmaceutical preparation used according to the invention preferably leads to a concentration of vWF of more than 2 units/ml blood over a time period of more than 24 hours, preferably more than 48 hours, for example measured as an antigen with a suitable ELISA. Furthermore, the effective amount on vWF should normalize the bleeding characteristic, i.e. the bleeding intensity should be clearly reduced and hemorrhage should be stopped in as short a time as possible after an injury, especially in less than 15 minutes, preferably less than 10 minutes.

In order to prevent the transmission of possibly present viruses, attention is to be paid that pharmaceutical preparations are preferably used which are treated for inactivation or depletion of viruses.

For inactivation of viruses, a heat treatment in solution and/or in solid state which can reliably inactivate lipid enveloped as well as non-lipid enveloped viruses is especially suitable. For example, the preparation according to the invention is heat treated according to EP 0 159 311 in a solid, wet state. Other methods for virus inactivation also encompass a treatment with detergents or chaotropic substances such as according to EP 0 519 901, WO 94/13329, DE 44 34 538, EP 0 131 740 and WO 90/15613.

The vWF is preferably employed as a highly pure protein which is obtained by a chromatographic purification process. The chromatographic purification especially is carried out by ion exchange chromatography and/or affinity chromatography. Materials for anion exchange, among them synthetic carrier materials or carriers based on carbohydrates with ligands, such as DEAE-, TMAE-, QAE-, Q- or amino alkyl groups and/or carriers with immobilized substances which have a specific affinity for vWF can be employed for this. Suitable affinity materials contain heparin, for example. This purification process is suitable, above all, for the large-scale isolation of rvWF. Attention should be paid to the fact that the vWF in the preparation according to the invention has a sufficient resistance against proteolytic degradation so that the addition of customary stabilizers can be avoided. However, in exceptional cases, a suitable protease inhibitor can also be added during the production process in order to maintain the intact structure. For further support of the stability of vWF, the pharmaceutical preparation can contain a polyalkylene glycol, such as PEG or polypropylene glycol or glycerin, in a concentration which does not precipitate the vWF and is pharmaceutically acceptable.

The formulation of the preparation used according to the invention can be carried out in a known and customary manner, for example with the aid of salts and, optionally, amino acids, but also in the presence of tensides. Preferably, salts such as, for example, sodium chloride or calcium chloride are used, and a pH in the range of 6–8 is chosen. Glycine or lysine are preferred as amino acids. Equally, a pharmaceutically acceptable buffer can be chosen. Due to the high stability of the vWF, the use of stabilizers such as carrier proteins or inhibitors can be typically avoided in the formulation.

Preferably, a rvWF is used in a preparation which has multimer bands in the absence of satellite bands after electrophoretic analysis. This corresponds to the structure of vWF as a non-fragmented, i.e. intact, protein. Preferably, the rvWF in the pharmaceutical preparation has the entire spectrum of multimers similar to the native multimer distribution, especially those of vWF with high molecular weight.

A further preferred preparation, however, contains a vWF fraction essentially consisting of vWF having a low molecular weight. It has proven that such a low molecular weight vWF, which does not contain the entire spectrum of multimers, is relevant in the preparation according to the invention. A vWF fraction composed of decamers and smaller oligomers, in particular a mixture of di- to hexamers, is preferred. Such a vWF fraction may be obtained by fractionation of a vWF containing solution according to the molecular weight and/or to the affinity to various chromatographic materials, whereby the separation of the low molecular weight vWF is possible.

The low molecular weight vWF fraction according to EP 0 705 846, for example, is obtained by affinity chromatography of rvWF using immobilized heparin. Likewise, it is possible to use functional defective multimers according to the low molecular product of Wagner et 1., The Journal of Cell Biology 101, 112–120 (1985).

The advantage of the vWF fraction having a molecular weight of lower than 5 million dalton, preferably lower than 3 million dalton, contained in the preparation according to the invention consists in the stabilization of Factor VIII in vivo essentially without the influence on the platelet aggregation and thereby on hemostatic and/or thrombotic processes. Such a preparation is especially suitable for the persistent stabilization of Factor VIII in vivo in a patient who should not be burdened with additional vWF activity and platelet aggregation activity. In an especially preferred embodiment, a vWF fraction is used which practically does not have any platelet binding activity, corresponding to a ratio of lower than 5 units ristocetin cofactor activity per 100 units antigen, preferably lower than 3 units per 100 units.

It has been shown that the low molecular weight rvWF fraction, for example, induced a Factor VIII level twice that of the level in a vWF deficient dog, which effect was persistent during the period of at least 48 hours. Simultaneously there was no change in the vWF plasma activity.

According to a preferred embodiment, the rvWF is obtained in a form which maintains the multimer pattern with a singulet structure after administration to a mammal. A proteolytic decomposition of the singlet into satellite bands is therewith absent.

The preferred concentration of vWF in the solution ready for administration is in the range of 1 to 100 units/ml. Due to the high purity of the preparation, this can also be formulated in concentrations of up to 1,000 U/ml. The activity is characterized by the ristocetin-mediated platelet aggregation and is given as ristocetin cofactor activity (RCoF) (for this, see Journal of Clinical Investigation 52, 2708–2716, 1973). The customary dose for the vWF lies in the range of 40 to 80 RCoF units/kg in intervals of 6–48 hours. As an initial dose, a higher dose up to 200 RCoF can also be chosen.

In a particular embodiment, the pharmaceutical preparation used according to the invention contains the vWF as the single essential component. Therewith, this preparation is essentially comprised of highly purified vWF.

For production of the pharmaceutical preparations, vWF can be purified from plasma or a plasma fraction, whereby the simultaneous enrichment or depletion of FVIII:C is suitable depending on the purpose. If one starts from a cell culture supernatant, the vWF can also be purified and concentrated in the presence or absence of FVIII:C. In this case, FVIII:C can either be added to the cell culture medium and/or co-expressed from the cells.

According to the invention, a diagnostic kit for determination of a phenotypic hemophilia A is further provided which comprises a) vWF in a pharmaceutically acceptable form and b) an agent for determining the FVIII:C activity in a blood sample of the patient.

Preferably, vWF with a prolonged half-life is used, especially vWF with a half-life of more than 20 hours. rvWF is especially well-suited for this purpose because it can be provided free of FVIII:C activity. In a human patient with phenotypic hemophilia A, the administration of a human vWF preparation causes the increase of endogenous FVIII:C content. This increase is more significant if the vWF stabilizes the FVIII:C in vivo according to the invention. However, in the case that the patient suffers from a defect of hemostasis which is caused by a lack of FVIII:C, such as hemophilia A, or in the case that the patient contains antibodies against FVIII:C which cause a lack of functionally active FVIII:C, the increase of endogenous FVIII:C is absent. Therewith, the vWF with the prolonged half-life can be used for the production of a diagnostic preparation which enables the differentiation between a vW disease and a vW disease with a simultaneous occurrence of a genomic defect with the effect of a lack of FVIII:C, especially hemophilia A.

The agent preferably comprises a reagent which contains an activator of blood coagulation and an agent for detection of blood coagulation.

The agent for determination of FVIII:C activity is either an agent for determining blood coagulation activity, whereby the blood coagulation time is measured (1-stage assay, or 2-stage assay), or a chromogenic test and/or a test for determining active blood coagulation enzymes which act depending on the FVIII:C activity of a sample. Preferably, a chromogenic test for the determination of the FVIII:C activity in a plasma or serum sample is carried out according to EP 0 496 723. As a chromogenic substrate, a substrate for factor Xa is employed in this case.

However, it is also possible to determine the FVIII:C activity with the aid of an aPTT (activated partial thromboplastin time) using a Factor VIII deficient plasma. The aPTT is an example for a test which induces the activation of coagulation with a suitable activator, whereby the extent of blood coagulation is detected with a suitable agent. The extent of blood coagulation can be detected for example by recording the coagulation time (end point determination) or the kinetics of blood coagulation.

The invention is further described by the following examples, which do not limit the invention.

EXAMPLE 1

Production of a Recombinant von Willebrand Factor from CHO Cells

A CHO cell clone which produces recombinant von Willebrand factor is produced as described in Fischer et al.

FEBS. Lett. 351:345–348, 1994. The cell line is brought to co-expression of human furin by transfection with a vector coding for the cDNA of human furin (van den Ouweland et al., Nucleic Acids Res. 18:664, 1990). Stable cell clones of this type were fermented on microcarriers in perfusion reactors on a large-scale (Blüml et al., IN: Spier R E, Griffith J B, Berthold W, Eds. Animal cell technology, Oxford, London:Butterworth-Heinemann, 1994:267–269).

The purification was carried out by a 2-step chromatographic method according to Thromb. Haemost. 73:1160, 1995. The fraction desorbed by elution with sodium chloride solution was isolated and rebuffered by gel filtration over Sephadex G25 (Pharmacia) in a buffer containing 5 g/ml $Na_3$citrate.$2H_2O$, 2 g/l NaCl, 5 g/l glycine, 5 g/l L-lysine.HCl and 0.62 g/l $CaCl_2.2H_2O$, pH 7.0. The preparation was characterized by a von Willebrand factor antigen content of 36.4 U/ml, measured in a commercial von Willebrand Factor ELISA (Boeringer Mannheim) and by a von Willebrand Factor activity of 13.8 U/ml, measured by means of ristocetin mediated platelet aggregation (Evans et al., Brit. J. Haematol. 37:289–294, 1977).

EXAMPLE 2
In Vivo Activity and Pharmacokinetics of Recombinant von Willebrand Factor in a Homozygote von Willebrand Factor Deficient Pig in Comparison to Porcine von Willebrand Factor For the examination, von Willebrand deficient animals are used, such as for example, the homozygote von Willebrand deficient pigs as described by Roussi et al., Brit. J. Haematol. 90:661–668, 1995. A four month old, 37 kg, female, homozygote von Willebrand-deficient pig was employed in this test. This was characterized by a bleeding time of over 30 minutes measured according to the ear bleeding method of Samama et al., Thromb. Haemostas. 71:663–669, 1994, and a von Willebrand Factor plasma level under the level of detection as determined by antigen ELISA as well as by the ristocetin-cofactor activity. The Factor VIII activity amounted to approximately 1 U/ml measured as human Factor VIII in the 1-stage coagulation assay (Immuno), 2-stage coagulation assay (Immuno) or chromogenic Factor VIII assay (Immunochrom FVIII:C, Immuno).

Figure 1:
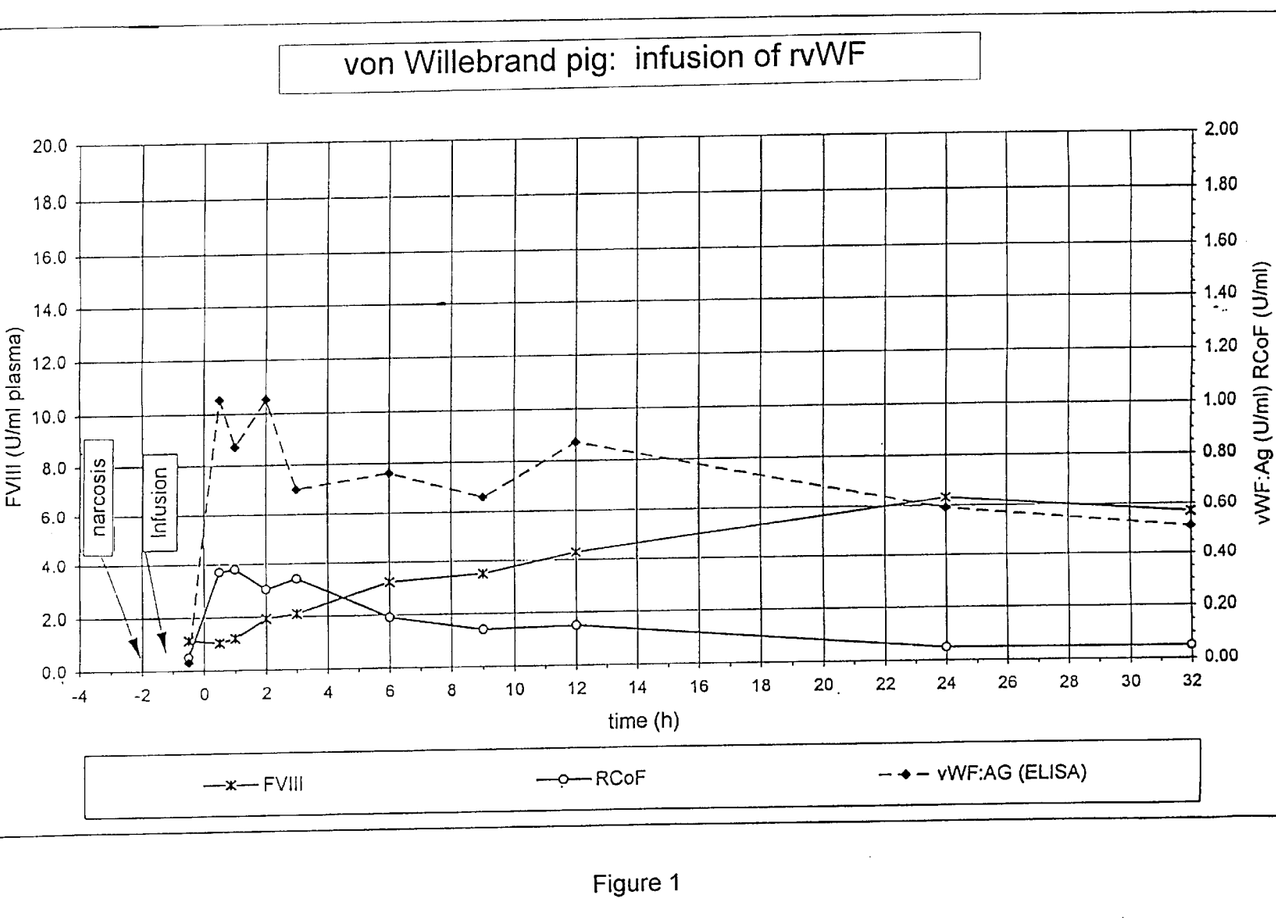
FIG. 1 depicts data regarding a course of coagulation parameters in a von Willebrand deficient pig after administration of a von Willebrand preparation according to the invention.

A preparation according to the invention which was obtained as described in example 1 was injected in a dose of 34 RCoF U/kg body weight into the pig under narcosis. Immediately before the infusion as well as 30 min, 1 h, 2 h, 3 h, 6 h, 9 h, 12 h, 24 h and 32 h after infusion, blood samples were taken, citrated plasma was produced therefrom, and von Willebrand Factor antigen, ristocetin cofactor activity and Factor VIII was determined from these samples according to the three above-named test methods. The results are to be taken from FIG. 1. It was shown that after approximately 24 hours, at a time point at which ristocetin-cofactor activity of the injected preparation was no longer detectable ex vivo, a sustained 5-fold increase in the plasma level of factor VIII appeared. For the vWF antigen, a biological half-life of 32.4 hours was calculated.

As a control, a porcine, plasmatic von Willebrand factor preparation was given in a dose of 45 RCoF U/kg body weight to the same pig immediately after taking the last blood sample. As after the addition of the preparation according to the invention, blood samples were taken at a time point 30 min, 1 h, 2 h, 3 h, 6 h, 9 h, 12 h, 24 h and 32 h after infusion, plasma was produced from these and the corresponding Factor VIII/von Willebrand Factor specific coagulation parameters were determined. It was shown that an induction of factor VIII also occurred here, which however, only attained a 2-fold value with respect to the starting value after approximately 10 hours and also decreased again more quickly. The porcine, plasmatic von Willebrand Factor showed a half-life time of approximately 10 hours. As a macroscopic parameter for the normalization of the disturbed coagulation system in the deficient animal, the bleeding time was determined which could be corrected from over 30 minutes before infusion of von Willebrand factor to approximately 13 minutes after infusion, whereby this effect was also detectable 32 hours after the infusion. The infusion of plasmatic von Willebrand Factor equally led to a correction of the bleeding time to approximately 15 minutes, whereas the bleeding time already corresponded to the starting value 24 h after the infusion of the plasmatic von Willebrand Factor preparation, i.e. no reduction could be achieved.

EXAMPLE 3
Pharmacokinetics of the Multimers Recombinant von Willebrand Factor in Pig From the plasma samples of the test from example 2, the structure of the von Willebrand Factor multimers was determined by SDS-agarose gel electrophoresis in a 2% agarose gel according to the method of Ruggeri et al., Blood 57:1140–1143. Thereby, the von Willebrand Factor multimers were made visible by an immunoenzymatic staining according to Aihara et al., Thromb. Haemostas. 55:263–267, 1986. As a primary antibody, a rabbit anti-von Willebrand Factor antiserum (Dakopatts, Glostrup, Denmark) was used at a dilution of 1:5,000. An alkaline phosphatase-conjugated affinity purified goat anti-rabbit-IgGH+L antibody (Axell, Accurate Chemical and Scientific Corp., NY) in a dilution of 1:1,000 served as a secondary antibody. The staining of the protein bands occurred by means of the nitro blue-tetrazolium-chloride bromo-indolyl-phosphate substrate system.

Before treatment with the preparation according to the invention, no von Willebrand Factor could be detected in the pig. After administration of the preparation, an atypical structure for the native state of a multimer pattern comprising singulets which is traceable to a non-proteolytically digested von Willebrand Factor was demonstrated. This structural property remained unchanged during the entire observation time period, i.e. no proteolytic degredation of the preparation occurred. However, the preparation was successively eliminated from the circulation corresponding to the pharmacokinetics. Multimers of the lowest molecular weight remained detectable up to 32 hours after infusion of the preparation.

Figure 2:
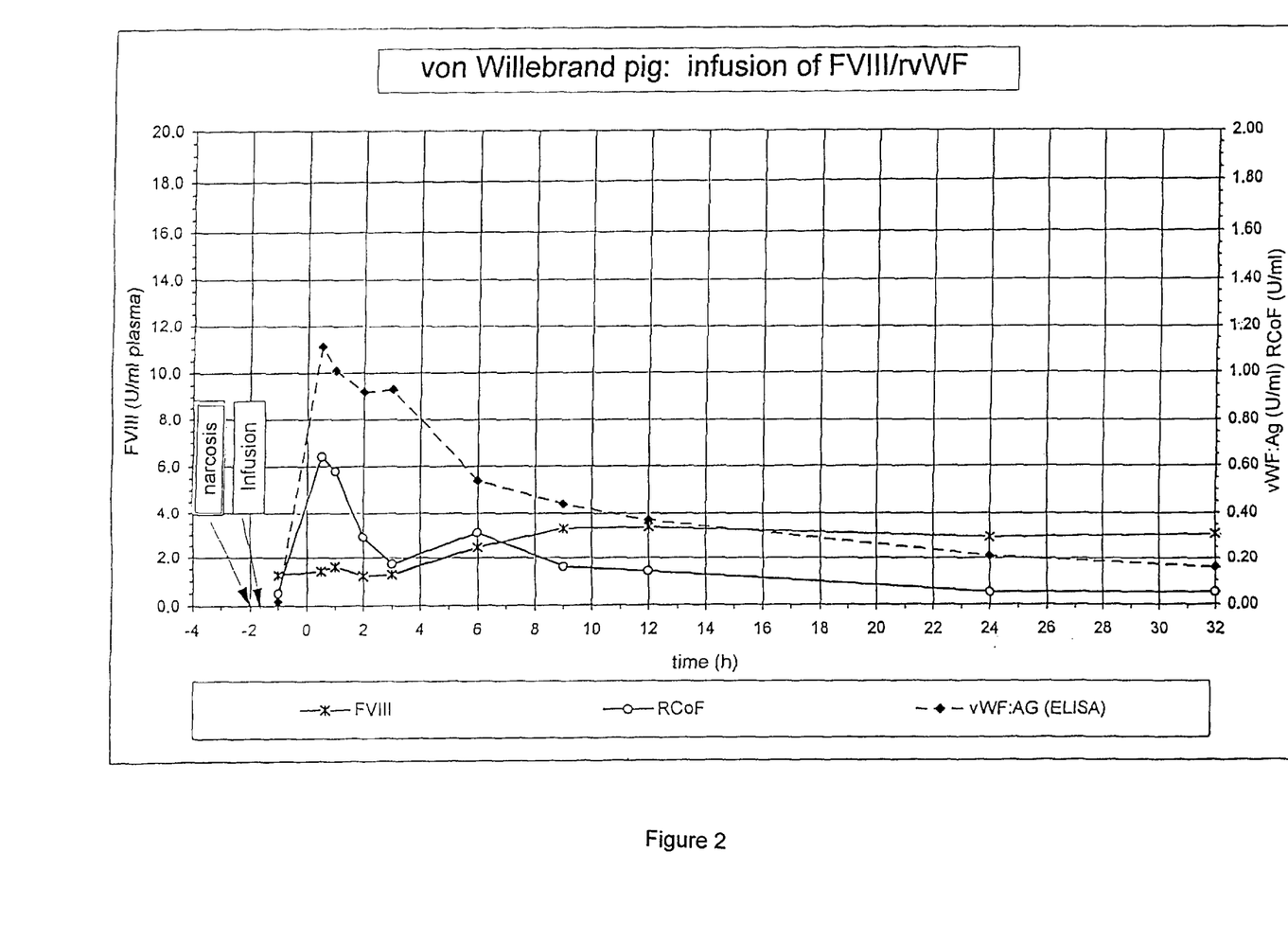
FIG. 2 depicts data regarding a course of coagulation parameters in a von Willebrand deficient pig after administration of a plasmatic vWF/Factor VIII concentrate.

EXAMPLE 4
In Vivo Activity and Pharmacokinetics of a Plasmatic von Willebrand/Factor VIII Concentrate in a Homozygote von Willebrand Factor Deficient Pig Analogously to Example 2, human plasmatic FVIII/vWF concentrate, HAEMATE HS 1000 (Fa. Behring), was given in a dosage of of 34 RCoF U/kg body weight to a 91 kg female, homozygotic, vWF deficient pig. This preparation is a factor VIII and von Willebrand Factor-containing concentrate. Correspondingly, a dose of 17 IU FVIII/kg body weight was administered to the pig together with the administration of the von Willebrand Factor. Immediately before the infusion as well as 30 min, 1 h, 2 h, 3 h, 6 h, 9 h, 12 h, 24 h and 32 h after the infusion, blood samples were taken, citrated plasma was produced and von Willebrand Factor antigen, ristocetin cofactor activity and Factor VIII was determined from these samples according to the test methods described in example 2. The results are to be taken from FIG. 2. It was shown that approximately 12 hours after the infusion of the preparation, at a time point where a measurable plasma level of the von Willebrand Factor ristocetin cofactor activity was still detectable, the FVIII plasma concentration was increased 2.8-fold. By external delivery of Factor VIII, the FVIII level increased immediately after the infusion by approximately 0.4 U/ml plasma. This corresponds to a theoretical recovery rate of 94% of the injected Factor VIII.

For vWF antigen, a biological half-time of 7.5 hours was calculated. Therewith, a clearly shorter biological half-life of the human plasmatic von Willebrand Factor was demonstrated in comparison to the recombinant von Willebrand Factor in example 2.

The multimer structure of the von Willebrand Factor in the pig plasma sample was analyzed analogously to example 3. The faster elimination from the circulation than that of recombinant von Willebrand Factor could also be detected here and was comparable to the antigen concentrations given in FIG. 2. The preparation showed the triplet structure typical to von Willebrand Factor which is attributable to a proteolytic degradation.

EXAMPLE 5
Comparison of the in Vivo Activity of a Plasmatic von Willebrand Factor/Factor VIII Concentrate and a Recombinant von Willebrand Factor in a Temporary von Willebrand Factor Deficient Mouse Female NMRI mice (approximately 20–30 g) were used and anesthetized by administration of 65 mg/kg pentobarbital. Subsequently, the bleeding characteristics are determined with a modified method according to Novak et al., Brit. J. Haemotol. 69:371–378, 1988 by defined injury of the tail tip. The blood emerging from the arterio-venous injury of the tail tip is collected on filters (Pipetman P5000 protection filter, Gilson) in such a manner that the blood can be directly dropped onto the filter without being drawn up by capillary action by the filter in order to prevent destruction of a forming blood clot. The filter units were changed every two minutes and the emerging blood was collected in fractions. The blood collection was carried out for 16 minutes. Thereafter, the wound was cauterized if the bleeding had not come to a stop. The qualification of the bleeding characteristics occurred by extracting the blood collected in fractions on the filters, each with 5 ml 0.4% ammonium hydroxide solution over 5 hours. Thereby, the erythrocytes which are collected with the blood in the filter are lysed. The hemoglobin is extracted by a 10 minute ultrasonic treatment (Sonorex RK100, Bandelin Electronic, Berlin) and quantitatively determined photometrically at 416 mm against a calibration curve. Such a curve can be established by pipeting mouse blood volumes between 10 μl–1 ml on the filter, extracting these as described above and photometrically determining the corresponding hemoglobin at 416 nm. Accordingly, linear calibration curves can be drawn up which permit a direct conversion of the hemoglobin concentration to the amount of blood per filter. The hemorrhage characteristic is determined by additively plotting the individual blood fractions against time. The course of bleeding of a healthy mouse is characterized under these conditions in that no further blood escapes from the artificially produced injury in an observation period between 6 min. and the end of the test, i.e. the bleeding already stops previously. In the graph, a curve of this type is distinguished by its parallelism to the x-axis (see FIG. 4).

Then mice are pretreated with an anti-von Willebrand Factor inhibitor in a dose of 10 ml/kg body weight. The anti-von Willebrand Factor inhibitor plasma is attained by immunization of an approximately 50 kg 1.5 year old goat with a von Willebrand Factor preparation as follows:

1 g cryoprecipitate is dissolved in 35 ml of a Tris/lysine-buffered NaCl solution (85 mM). Proteins of the prothrombin complex are removed by adsorption on $AlOH_3$ and $BaSO_4$. In this connection, the solution containing von Willebrand Factor/Factor VIII is incubated with 0.1% by weight $AlOH_3$ for 1 h at 22° C.

Subsequently, the $AlOH_3$-protein complex is separated by centrifugation. The supernatant obtained is incubated further with 0.1% by weight $BaSO_4$ under stirring and the $BaSO_4$-protein complex is separated again by centrifugation. The supernatant is subsequently adjusted to pH 6.8 and purified by chromatography over Q-Sepharose® FF (Pharmacia). The von Willebrand Factor complex is adsorbed to the gel packed in a column; non-binding proteins are removed by washing with 4 column volumes of starting buffer. The elution of the protein fraction is carried out with a buffer (50 mM Tris/HCl, 500 mM NaCl, pH 6.8). The eluate obtained is diluted to a concentration of 175 mM NaCl with 50 mM Tris/HCl buffer, pH 6.8, and subsequently further purified by gel filtration on Sepharose® CL6B (Pharmacia). The gel filtration is carried out with a linear flow of 5.7 cm/h in a column with 26 mm diameter and a bed height of 82 cm. The protein fraction of the exclusion volume is detected UV-spectroscopically at 280 nm. The protein peak of the exclusion volume is concentrated by ultrafiltration with an ultrafilter with a retention size of 30,000 D. A von Willebrand Factor/Factor VIII complex produced in this manner had a specific activity of 173 ristocetin-cofactor units (U RCoF) vWF/mg protein (determined by means of protein determination according to Bradford, Anal. Biochem. 72:248–254, 1976). The preparation is free from coagulation factors II, VII, IX, X, XI and XII.

Figure 3:
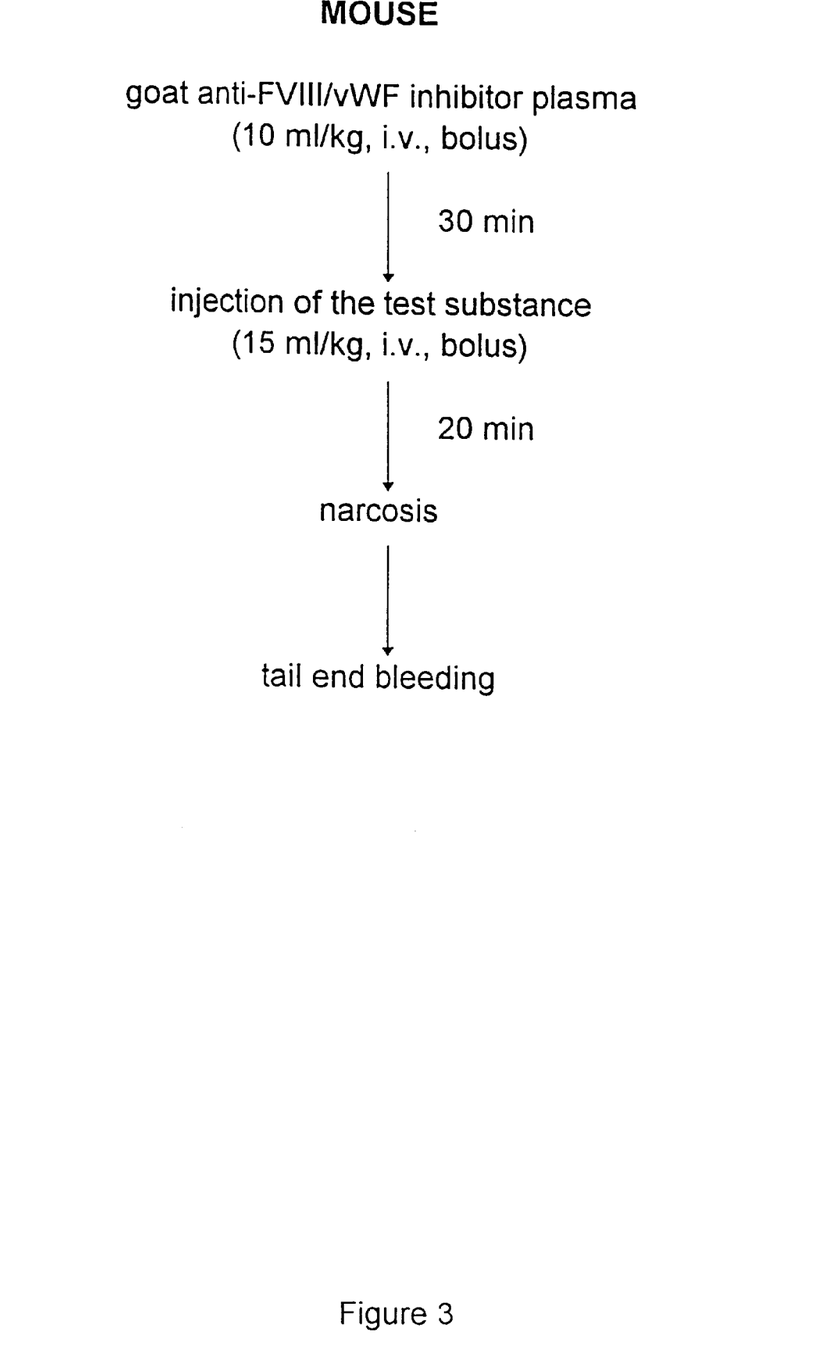
FIG. 3 depicts an administration methodology for a mouse depleted of von Willebrand Factor.

Then, mice are pretreated with the anti-von Willebrand Factor inhibitor plasma according to the scheme in FIG. 3. The characteristics of tail tip bleeding in a mouse with induced temporary von Willebrand deficiency of this type after infusion of physiological sodium chloride solution comprise constant bleeding from the beginning of the measurement interval to the end of the experiment (see FIG. 4). In this model of von Willebrand/Jürgens Syndrome, a preparation containing plasmatic von Willebrand Factor as well as a preparation according to the invention are then examined for their effect. In this connection, 100 U vWF ristocetin cofactor activity (RCoF)/kg is given in both cases, each as a bolus. The bleeding characteristics are to be taken from FIG. 4. Surprisingly, it is shown that a von Willebrand Factor preparation produced according to example 1 corrects the bleeding characteristics of the von Willebrand-deficient mouse to that of a healthy mouse in this test, whereas the plasmatic von Willebrand Factor preparation (IMMUNATE® STIM4, Immuno) causes a clear reduction of the bleeding intensity in the same dosage, but does not lead to a cessation of bleeding as does the preparation according to the invention. After administration of the recombinant von Willebrand Factor preparation and determination of the bleeding characteristics, a blood sample was taken from the animals by heart puncture. The multimer composition of the injected vWF was determinied from ex vivo plasma samples. It was shown that the singlet structure was also maintained after infusion over the entire measurement time period.

Figure 5:
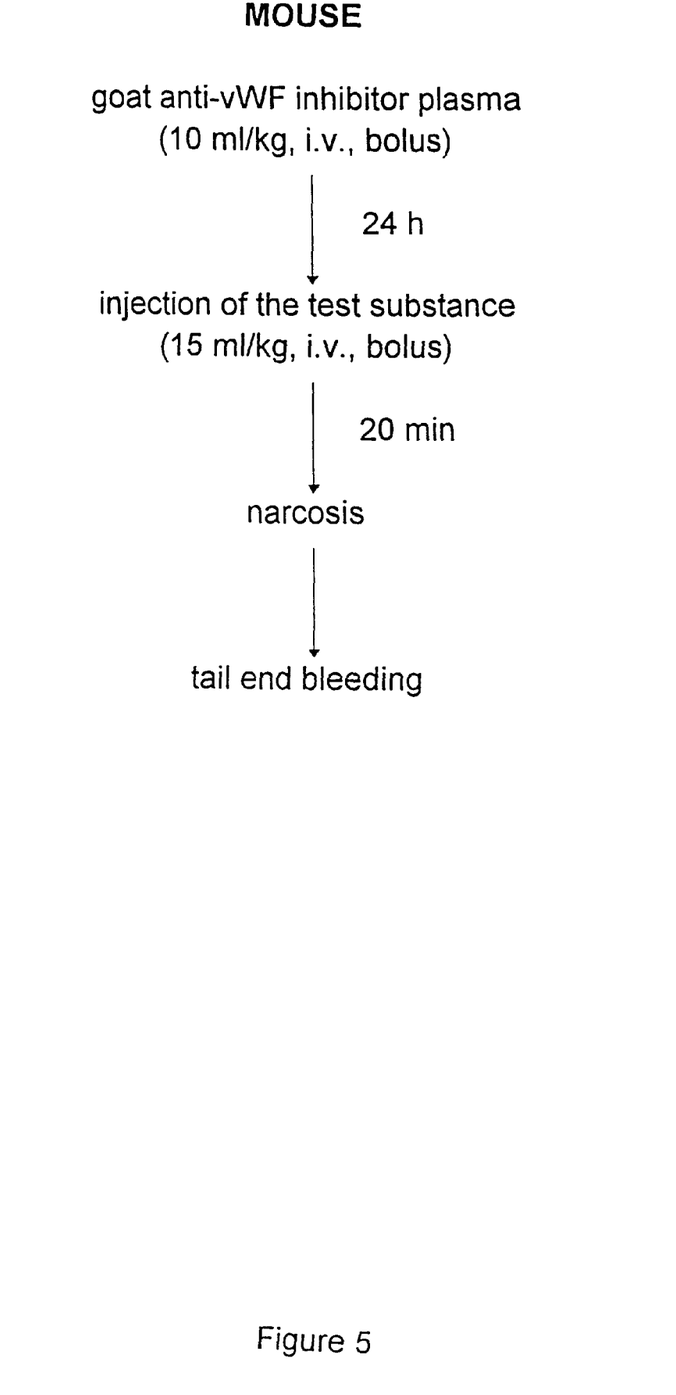
FIG. 5 depicts the administration methodology for a mouse depleted of von Willebrand Factor according to Example 6.

EXAMPLE 6
Pharmaceutical Preparation Containing Recombinant vWF/FVIII Complex in a Temporary von Willebrand Factor Deficient Mouse Female NMRI mice, approximately 20–30 g, are treated analogously to example 5 with an anti-vWF inhibitor plasma which was obtained by immunizing a goat with a recombinant vWF. The vWF anti-plasma resulting from the immunization cross-reacts with mouse vWF in vitro and in vivo. With administration of an anti-vWF-containing anti-plasma in a dose of 10 ml/kg as an i.v. bolus injection, a clear reduction of the vWF antigen plasma level in the mouse already results 1 hour after administration; however, the FVIII plasma concentration is first reduced to approximately 50% of the normal value in contrast to a treatment with an anti-vWF inhibitor from example 5. Since the anti-plasma used contains no antibodies against FVIII, this effect is a secondary effect of vWF immunedepletion. When mice are treated with the same anti-vWF inhibitor plasma and a delay of 24 hours is abided by, the vWF plasma level is diminished to under the level of detection, and, as a secondary effect of the induced vWF deficiency, the FVIII plasma concentration is also diminished to ≦10% of the normal value. Connected with this, a significant increase of the tendency to hemorrhage results which is measured by the tail bleeding characteristics as in example 5. Then, in groups of 10 animals each, mice pre-treated with anti-vWF anti-plasma in this manner were treated after a delay of 24 hours either with buffer as a control or with rvWF in increasing doses of 20, 100, 200 and 400 RCoF U/kg (see treatment scheme, FIG. 5). Equally, mice were treated with rFVIII (Recombinate®, Baxter) in doses of 920 and 1840 U/kg and mice were treated with a pharmaceutical composition containing rvWF and rFVIII in doses of 100 vWF RCoF U and 460 FVIII U/kg as well as 200 vWF RCoF U in combination with 920 FVIII U/kg. The bleeding characteristics of all mice in relation to healthy mice were determined as described in Example 5. The results are summarized in FIG. 6.

Figure 4:
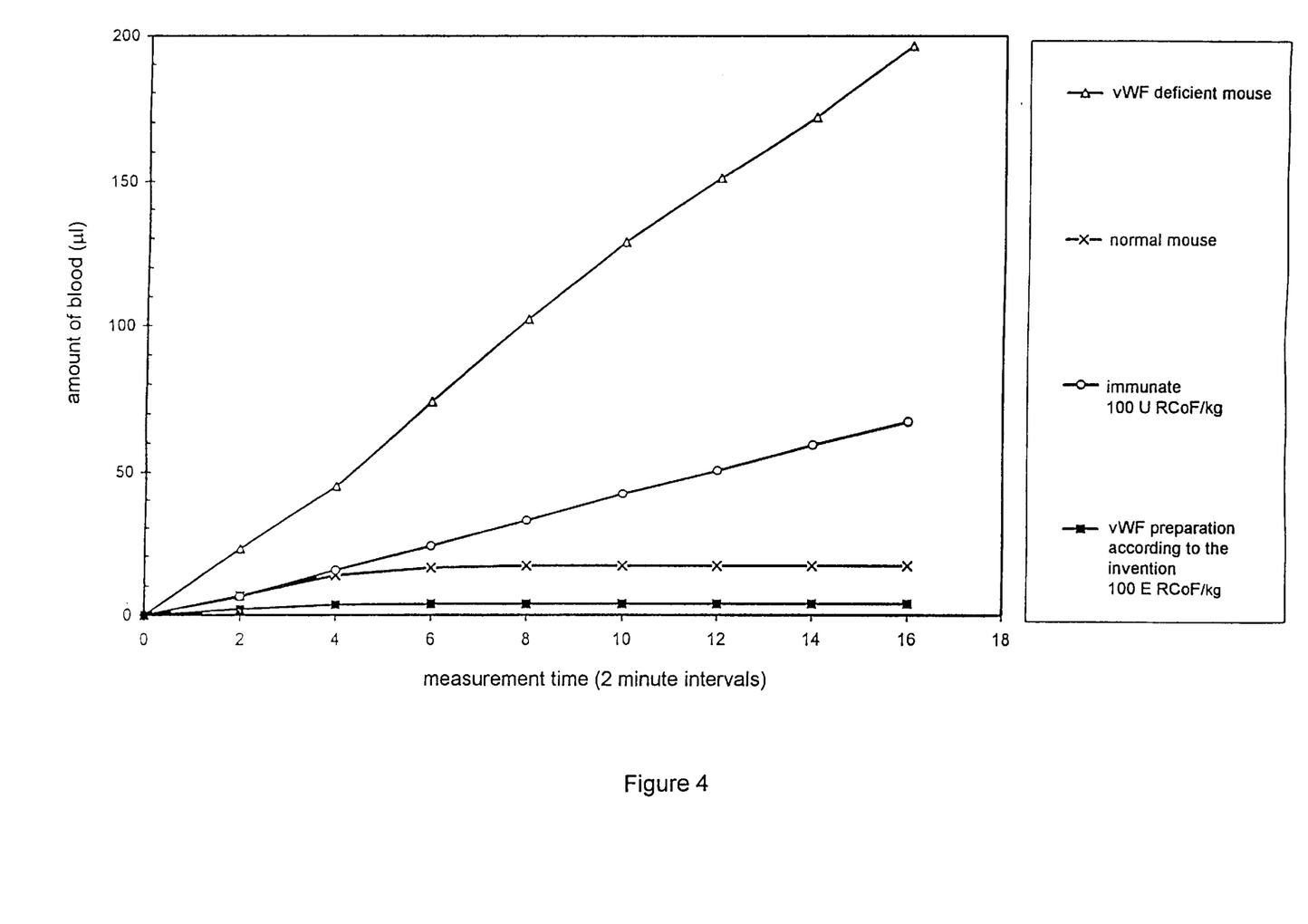
FIG. 4 depicts data relating to the hemorrhage characteristics of von Willebrand deficient mice after administration of plasmatic von Willebrand Factor (100 U RCoF/kg body weight) or a preparation according to the present invention (100 U RCoF/kg body weight). Data from normal mice and mice with vWF deficiency (without administration) also are depicted.
Figure 6:
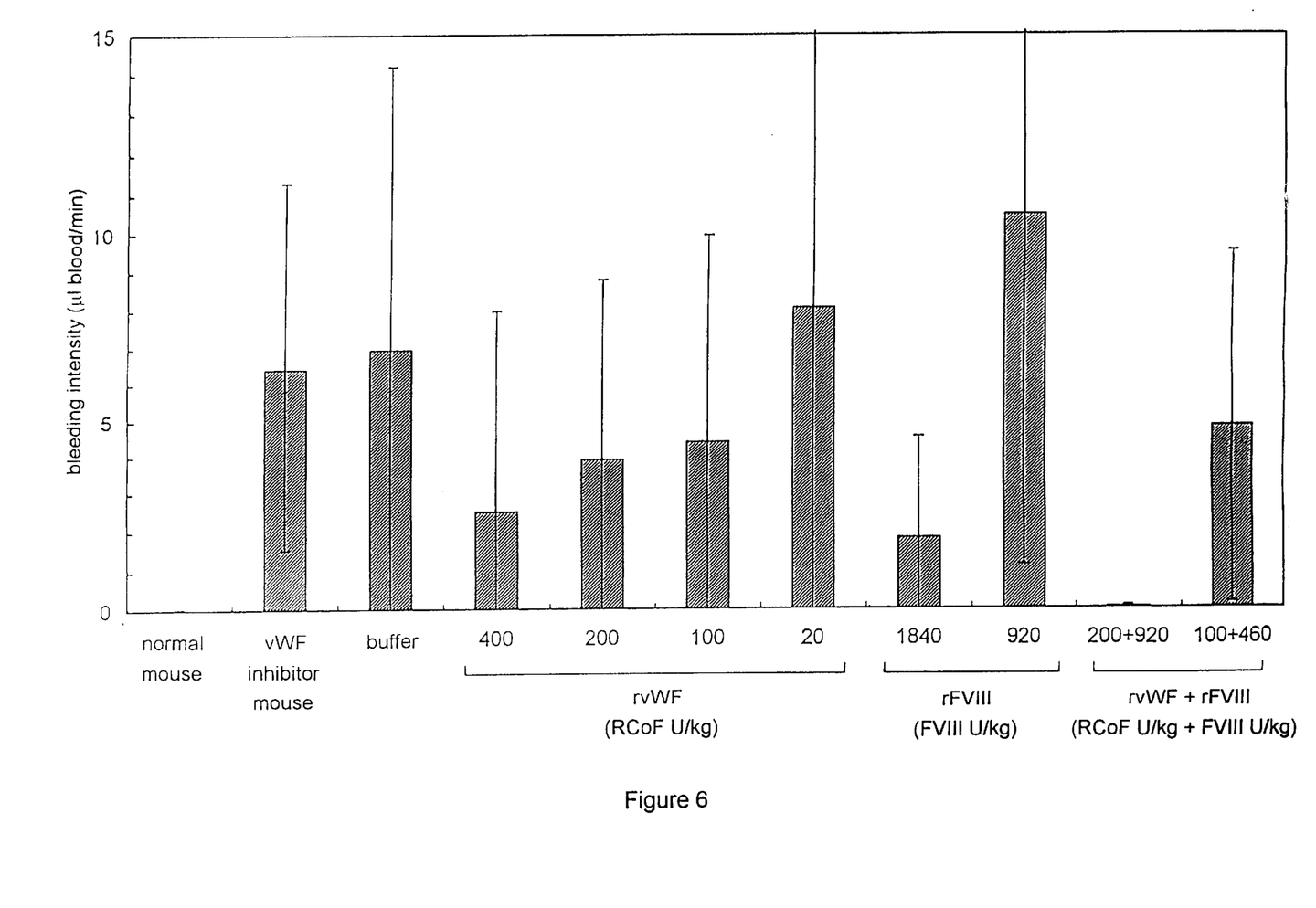
FIG. 6 depicts data relating to the hemorrhage behavior of von Willebrand Factor deficient immune-depleted mice after administration of recombinant von Willebrand Factor and recombinant Factor VIII in comparison to normal mice and mice with vWF deficiency (without administration).

The bars represent the bleeding intensity which was measured in the course of the tail-end bleeding experiments, whereby the bleeding intensity is defined as the increase of the bleeding characteristic curves, as they are defined in FIG. 4, in time intervals between 6 and 16 min. Recombinant vWF leads to a clear reduction of the bleeding intensity in increasing doses. However, in contrast to that described in example 5, no normalization of the bleeding behavior results in this mouse model. Recombinant FVIII equally leads to a clear reduction of the bleeding behavior with increasing doses, but does not lead to a complete normalization of the bleeding behavior. Only the combination of rvWF with rFVIII in a dose of 200 vWF RCoF U and 920 FVIII U/kg leads to a complete normalization of the abnormally increased bleeding behavior.

EXAMPLE 7 vWF in a Dog with Severe von Willebrand's Disease

A fraction containing recombinant low molecular weight von Willebrand factor (LMW-rvWF) was obtained by chromatography on immobilized heparin following EP 0 705 846. Recombinant von Willebrand factor as described in example 1 served as a starting material. The resulting low molecular weight fraction of rvWF was formulated in a buffer containing 5 g/l sodium citrate.2H$_2$O, 2 g/l NaCl, 5 g/l glycine, 5 g/l l-lysine hydrochloride, 0.62 g/l calcium chloride.2H$_2$O, pH 7.0. This preparation had a vWF-antigen content of 200 U/ml and a very low vWF ristocetin cofactor activity of 3 U/ml. The multimer characterization on 2% agarose SDS-gel electrophoresis showed that the preparation mainly contained di-, tetra- and hexamers of the vWF monomers.

Figure 7:
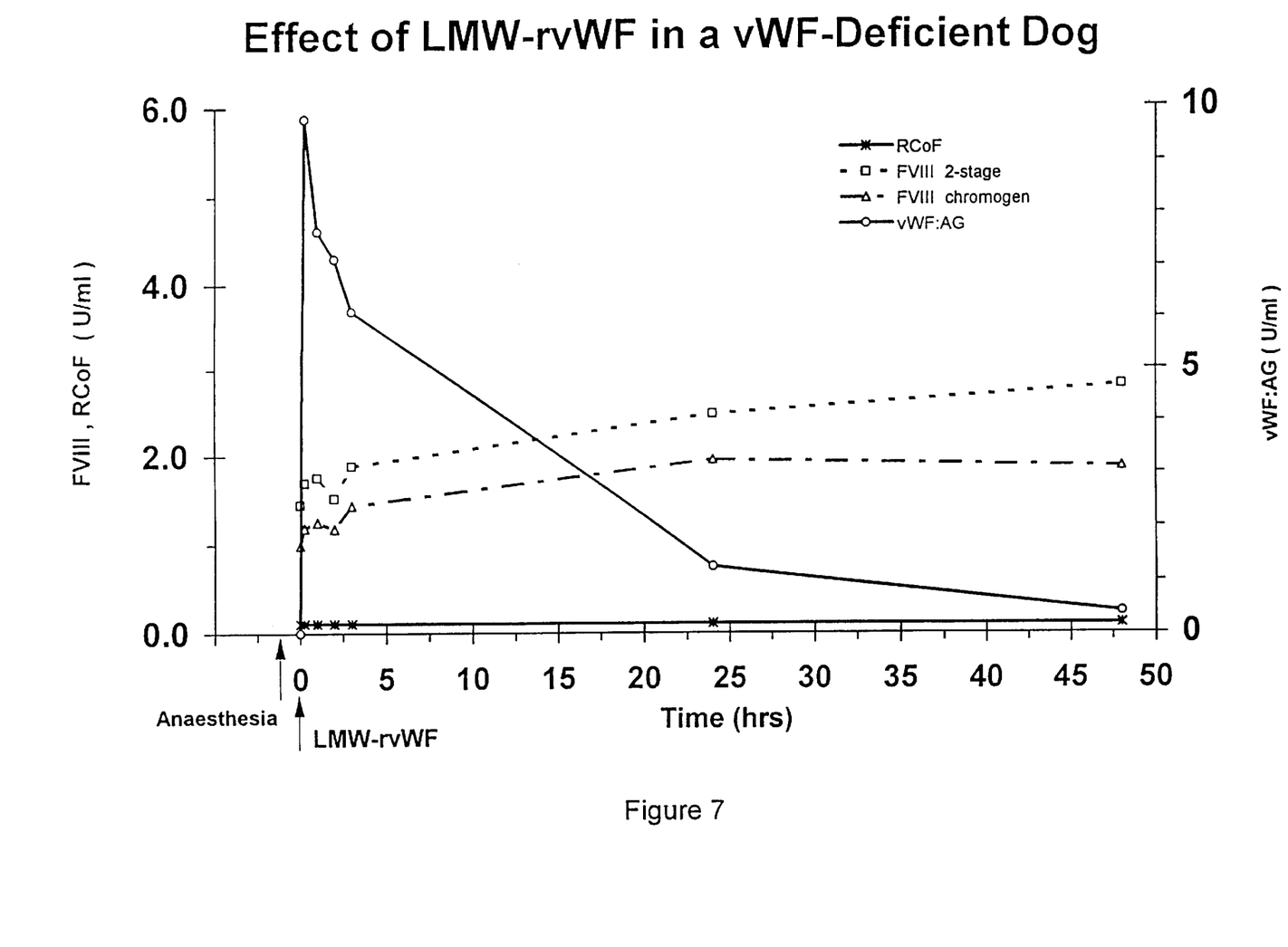
FIG. 7 depicts data relating to the effect of low molecular weight von Willebrand Factor in a von Willebrand Factor deficient dog.

A female vWF-deficient dog with 9 kg bodyweight, a vWF plasma antigen below detection limit and a Factor VIII plasma activity of 50% of the normal value, was anesthetized and infused with the low molecular weight von Willebrand factor preparation at a dose of 450 U/kg bodyweight equivalent to 45 mg vWF:Ag/kg bodyweight. Prior to infusion and at time points, 15 min, 30 min, 1 h, 2 h, 3 h, 24 h and 48 h post infusion of the low molecular weight vWF, plasma samples were taken and analyzed for vWF:Ag, ristocetin cofactor activity and FVIII activity, measured in the 2-stage and chromogenic assay. The results are shown in FIG. 7. Plasma samples were also analyzed with agarose gel electrophoresis as described in example 3 and the vWF oligomers were monitored over time.

VWF oligomers were cleared from the circulation with disappearance of the higher molecular weight forms first. FIG. 7 shows that although vWF:Ag was gradually eliminated from the circulation, Factor VIII activity increased, reached approx. 200% of the starting level 24 h post infusion and remained stable at this level at least for the next 24 h, while vWF:Ag and oligomers had disappeared completely from the circulation. At none of the time points, when plasma fractions were taken from the animal, could vWF activity expressed in ristocetin cofactor units be measured.

The results demonstrated that a vWF lacking platelet binding activity was able to stabilize and induce plasma FVIII activity thus triggering intrinsic coagulation.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein.

We claim:

1. A pharmaceutical preparation that increases the blood coagulation Factor VIII level consisting essentially of recombinantly-produced von Willebrand Factor (vWF), wherein the vWF (i) are multimers composed of singlets and (ii) have a prolonged in vivo circulatory half-life of more than 20 hours.

2. A pharmaceutical preparation according to claim 1, wherein the vWF has the entire spectrum of multimers similar to the native multimer distribution.

3. A pharmaceutical preparation according to claim 1, wherein the vWF has a molecular weight less than 5 million daltons.

4. A pharmaceutical preparation according to claim 1, wherein the preparation is in a ready-to-administer solution that has a vWF concentration of 1 to 1,000 U/ml.

5. A pharmaceutical preparation according to claim 1, wherein the vWF has been purified chromatographically.

6. A pharmaceutical preparation according to claim 1, wherein at least 80% of the vWF is processed by contact with a vWF-processing protease.

7. A pharmaceutical preparation according to claim 1, wherein the vWF has an in viva circulatory half-life of more than 30 hours.

8. A pharmaceutical preparation according to claim 6, wherein the vWF-processing protease is selected from the group consisting of furin and subtilisin-like enzymes.

9. A pharmaceutical composition according to claim 1, wherein the vWF is expressed in a mammalian cell that also expresses a vWF-processing protease that is selected from the group consisting of furin and subtilisin-like enzymes.

10. A pharmaceutical composition according to claim 9, wherein the mammalian cells are CHO cells.

11. A pharmaceutical preparation that increases the blood coagulation Factor VIII level consisting essentially of recombinant von Willebrand Factor (vWF), wherein the vWF (i) are multimers composed of singlets and (ii) have a prolonged in vivo circulatory half-life of more than 20 hours and is obtainable by expressing in a mammalian cell a polynucleotide encoding vWF and a polynucleotide encoding a vWF-processing protease that is selected from the group consisting of furin and subtilisin-like enzymes.

12. A pharmaceutical composition according to claim 11, wherein the mammalian cells are CHO cells.

13. A pharmaceutical preparation that increases the blood coagulation Factor VIII level, wherein the preparation consists essentially of recombinantly-produced von Willebrand Factor (vWF), wherein the vWF (i) are multimers composed of singlets and (ii) have an in vivo circulatory half-life of at least 30 hours.

14. A pharmaceutical preparation that increases the blood coagulation Factor VIII level in a mammal, wherein the preparation consists essentially of recombinantly-produced and proteolytically-processed von Willebrand Factor (vWF), (i) are multimers composed of singlets and (ii) have an in vivo circulatory half-life of at least 20 hours.

15. A pharmaceutical preparation according to claim 1, wherein the vWF has a molecular weight that is no more than 5 million daltons.

* * * * *

UNITED STATES PATENT AND TRADEMARK OFFICE
CERTIFICATE OF CORRECTION

PATENT NO. : 6,005,077
DATED : December 21, 1999
INVENTOR(S) : Hans-Peter Schwarz et al.

It is certified that error appears in the above-identified patent and that said Letters Patent is hereby corrected as shown below:

Title page,
"[73] Assignee: Immuno Aktiengesellschaft, Vienna, Austria", and insert the following: -- [73] Assignee: Baxter Aktiengesellschaft, Vienna, Austria --.

Signed and Sealed this

Thirtieth Day of April, 2002

Attest:

JAMES E. ROGAN
Attesting Officer        Director of the United States Patent and Trademark Office